US011033299B2

(12) United States Patent
Silver

(10) Patent No.: US 11,033,299 B2
(45) Date of Patent: Jun. 15, 2021

(54) MULTIMODAL SURGICAL GAS DELIVERY SYSTEM HAVING CONTINUOUS PRESSURE MONITORING OF A CONTINUOUS FLOW OF GAS TO A BODY CAVITY

(71) Applicant: Conmed Corporation, Utica, NY (US)

(72) Inventor: Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 304 days.

(21) Appl. No.: 15/812,649

(22) Filed: Nov. 14, 2017

(65) Prior Publication Data

US 2018/0132895 A1 May 17, 2018

Related U.S. Application Data

(60) Provisional application No. 62/421,480, filed on Nov. 14, 2016.

(51) Int. Cl.
*A61B 17/34* (2006.01)
*A61M 13/00* (2006.01)
(Continued)

(52) U.S. Cl.
CPC ...... *A61B 17/3474* (2013.01); *A61B 17/3421* (2013.01); *A61M 13/006* (2014.02);
(Continued)

(58) Field of Classification Search
CPC ............ A61B 17/3474; A61B 17/0218; A61B 17/3421; A61M 2205/3344;
(Continued)

(56) References Cited

U.S. PATENT DOCUMENTS 4,735,603 A * 4/1988 Goodson ................ A61B 18/20
600/560
4,874,362 A 10/1989 Wiest et al.
(Continued)

FOREIGN PATENT DOCUMENTS

DE 4219859 A1 12/1993
EP 2482869 A1 8/2012
(Continued)

OTHER PUBLICATIONS

Supplemental Search Report dated Sep. 8, 2014 in connection with EP Application No. 11827365.
(Continued)

*Primary Examiner* — Lauren P Farrar
*Assistant Examiner* — Hamza A Darb
(74) *Attorney, Agent, or Firm* — Locke Lord LLP; Scott D. Wofsy

(57) ABSTRACT

A system is disclosed for delivering insufflation gas to a body cavity of a patient during an endoscopic surgical procedure, which includes an insufflation conduit for delivering a continuous flow of insufflation gas to the body cavity at a flow rate through a flow path that communicates with a pneumatically sealed trocar which prevents over-pressurization of the body cavity, and an insufflator for driving gas flow through the insufflation conduit at a driving pressure, wherein the system can be configured so that either the gas flow rate through the insufflation conduit or the driving pressure required to maintain the specified flow rate can vary depending upon body cavity pressure.

6 Claims, 5 Drawing Sheets

(51) Int. Cl.
*A61B 17/02* (2006.01)
*A61M 1/00* (2006.01)

(52) U.S. Cl.
CPC ..... *A61B 17/0218* (2013.01); *A61B 2218/008* (2013.01); *A61M 1/0031* (2013.01); *A61M 2205/33* (2013.01); *A61M 2205/3334* (2013.01); *A61M 2205/3344* (2013.01); *A61M 2205/3569* (2013.01); *A61M 2205/3584* (2013.01); *A61M 2205/3592* (2013.01); *A61M 2205/502* (2013.01); *A61M 2205/75* (2013.01); *A61M 2210/1021* (2013.01)

(58) Field of Classification Search
CPC .............. A61M 13/003; A61M 1/0029; A61M 1/0025; A61M 13/006; A61M 2205/33; A61M 2218/008; A61M 1/0031; A61M 2205/334; A61M 13/00; A61M 5/1684; A61M 5/48; A61M 2025/0001
See application file for complete search history.

(56) References Cited

U.S. PATENT DOCUMENTS

| | | | |
|---|---|---|---|
| 6,269,813 B1 * | 8/2001 | Fitzgerald | A61M 16/20 128/207.16 |
| 6,299,592 B1 | 10/2001 | Zander | |
| 6,402,714 B1 * | 6/2002 | Kraft-Kivikoski | A61M 13/003 600/560 |
| 7,182,752 B2 | 2/2007 | Stubbs et al. | |
| 7,250,035 B1 | 7/2007 | Ott et al. | |
| 7,285,112 B2 | 10/2007 | Stubbs et al. | |
| 7,338,473 B2 | 3/2008 | Campbell et al. | |
| 7,413,559 B2 | 8/2008 | Stubbs et al. | |
| 7,854,724 B2 | 12/2010 | Stearns et al. | |
| 8,715,219 B2 | 5/2014 | Stearns et al. | |
| 8,795,223 B2 | 8/2014 | Stearns et al. | |
| 8,961,451 B2 | 2/2015 | Stearns et al. | |
| 9,067,030 B2 | 6/2015 | Stearns et al. | |
| 9,095,372 B2 | 8/2015 | Stearns et al. | |
| 9,295,490 B2 | 3/2016 | Stearns et al. | |
| 9,375,539 B2 | 6/2016 | Stearns et al. | |
| 9,526,849 B2 | 12/2016 | Stearns et al. | |
| 9,526,886 B2 | 12/2016 | Mastri et al. | |
| 2005/0140759 A1 | 6/2005 | Hilton et al. | |
| 2005/0234391 A1 * | 10/2005 | Uesugi | A61M 13/003 604/24 |
| 2007/0088275 A1 * | 4/2007 | Stearns | A61B 17/3423 604/164.01 |
| 2007/0249990 A1 | 10/2007 | Cosmescu | |
| 2009/0240192 A1 | 9/2009 | Power et al. | |
| 2010/0185139 A1 | 7/2010 | Stearns et al. | |
| 2013/0267892 A1 * | 10/2013 | Woolford | A61M 3/0258 604/34 |

FOREIGN PATENT DOCUMENTS

| | | |
|---|---|---|
| JP | 2005-287840 A | 10/2005 |
| JP | 2016-052478 A | 4/2016 |
| KR | 20120015598 A | 2/2012 |
| WO | 20100042204 A2 | 4/2010 |
| WO | 201141387 A1 | 4/2011 |

OTHER PUBLICATIONS

Translation of Office Action for Japanese Patent Application No. JP2013-529418, dated Jun. 23, 2015.
International Search Report issued in corresponding PCT Patent Application No. PCT/US2017/061490, dated Feb. 27, 2018.

* cited by examiner

MULTIMODAL SURGICAL GAS DELIVERY SYSTEM HAVING CONTINUOUS PRESSURE MONITORING OF A CONTINUOUS FLOW OF GAS TO A BODY CAVITY

CROSS-REFERENCE TO RELATED APPLICATION

The subject application claims the benefit of priority to U.S. Provisional patent application Ser. No. 62/421,480 filed Nov. 14, 2016, the disclosure of which is herein incorporated by reference in its entirety.

BACKGROUND OF THE INVENTION

1. Field of the Invention

The subject invention relates to surgical gas delivery systems, and more particularly, to multimodal gas delivery systems for surgical insufflation, smoke evacuation and/or recirculation, which is also configured for continuous pressure monitoring of a continuous flow of gas to a body cavity.

2. Background of the Related Art

Minimally invasive surgical techniques such as endoscopic and laparoscopic surgical procedures have become increasingly common. Benefits of such procedures include reduced trauma to the patient, reduced opportunity for infection and decreased recovery time. Laparoscopic surgical procedures within the abdominal (peritoneal) cavity are typically performed through a device known as a trocar or cannula, which facilitates the introduction of surgical instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by way of a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the inserter is removed, and the trocar allows access for instruments to be inserted into the abdominal cavity. Typical trocars provide a way to insufflate the abdominal cavity, so that the surgeon has an open interior space in which to operate and work.

The trocar must maintain the pressure within the abdominal cavity by providing a seal between the trocar and any surgical instrument being passed therethrough, while still allowing at least a minimum freedom of movement of the surgical instruments. Such instruments can include, for example, scissors, grasping instruments, and occluding instruments, cauterizing units, cameras, light sources and other surgical instruments.

Sealing elements or mechanisms are typically provided within trocars to prevent the escape of insufflation gas. These typically include a duckbill-type valve made of a relatively pliable material, to seal around an outer surface of surgical instruments passing through the trocar.

Surgical access devices or trocars that permit sealed access to an insufflated surgical cavity without the need for conventional mechanical seals are known in the art. These devices are adapted and configured to provide sealable access to a surgical cavity through the use of a pneumatic or gaseous seal generated and maintained by a circulating flow of pressurized insufflation gas. Such devices are described in U.S. Pat. Nos. 7,854,724 and 8,795,223, the disclosures of which are herein incorporated by reference in their entireties. Also known in the art are multimodal surgical gas delivery systems that are used in conjunction with such pneumatically sealed trocars for delivering insufflation gas to a body cavity, for circulating surgical gas through the trocar to generate and maintain the pneumatic seal and for facilitating smoke evacuation from the body cavity.

Use of a multimodal system helps to reduce costs by requiring purchase of only one system, while achieving multiple functions, and also thereby reduces the amount of equipment needed in an operating room, thus reducing clutter and allowing space for other necessary equipment. Such systems are described for example in U.S. Pat. Nos. 8,715,219 and 8,961,451 as well as in U.S. Pat. Nos. 9,295,490 and 9,375,539, the disclosures of which are all herein incorporated by reference in their entireties.

In certain applications, it is advantageous to monitor pressure at body cavity, for example, the abdominal cavity, in real time during insufflation. Real time pressure monitoring helps to better detect and respond to changes in pressure at surgical site within the body cavity. Conventional methods of continuously monitoring surgical cavity pressure, such as the one disclosed in U.S. Pat. No. 6,299,592, separate insufflation and pressure monitoring, requiring a dedicated pressure sensing lumen, port, or connection to the body cavity.

The systems described herein do not require a dedicated pressure sensing lumen or connection, and instead, utilize the consistent flow of new or recirculated insufflation gas being provided to the surgical cavity. Furthermore, because it is not necessary to stop the flow of new insufflation gas to the surgical cavity to sense pressure, the systems disclosed herein provide improved smoke removal by recirculating gas through a pneumatically sealed access device.

SUMMARY OF THE INVENTION

The subject invention is directed to a new and useful system for delivering insufflation gas to a body cavity of a patient during an endoscopic or laparoscopic surgical procedure. In one embodiment of the invention, the system includes an insufflation conduit for delivering a continuous flow of insufflation gas to the body cavity of a patient at a variable flow rate through a flow path that communicates with a pneumatically sealed trocar which prevents overpressurization of the body cavity, and an insufflator for driving gas flow through the insufflation conduit at a given driving pressure, wherein the gas flow rate through the insufflation conduit will vary depending upon body cavity pressure. This system further includes a flow meter communicating with the insufflation conduit and located between the insufflator and the body cavity for continuously measuring gas flow through the insufflation conduit, and a processor for determining a body cavity pressure corresponding to a given driving pressure based upon a gas flow measurement from the flow meter.

Preferably, the processor relies upon data stored in memory in a look up table based upon a known resistance characteristic of the flow path, and it utilizes a calibration algorithm to determine the resistance characteristic of the flow path when it is initially unknown. The system further includes a pressure sensor located along the flow path for taking periodic static pressure measurements and associating those static pressure measurements with periodic flow measurements.

In another embodiment of the subject invention, the system includes an insufflation conduit for delivering a continuous flow of insufflation gas to the body cavity of a patient at a specified flow rate through a flow path that communicates with a pneumatically sealed trocar which prevents over-pressurization of the body cavity, and an insufflator for driving gas flow through the insufflation conduit at a variable driving pressure, wherein the driving pressure required to maintain the specified flow rate will vary depending upon body cavity pressure. This system further includes a driving pressure sensor communicating with the insufflation conduit and located between the insufflator and the body cavity for continuously measuring variable driving pressure in the insufflation conduit, and a processor for determining an amount of driving pressure required to maintain the specified flow rate of insufflation gas to the body cavity through the flow path. The processor is also configured to determine a body cavity pressure corresponding to a given gas flow rate based upon a driving pressure measurement from the driving pressure sensor.

The processor relies upon data stored in memory in a look up table based upon a known resistance characteristic of the flow path, and it utilizes a calibration algorithm to determine the resistance characteristic of the flow path when it is initially unknown. The system further includes a flow meter that provides feedback to the insufflator so that the insufflator can maintain the specified flow to the body cavity. The system also includes a second pressure sensor located along the flow path for taking periodic static pressure measurements and associating those static pressure measurements with periodic driving pressure measurements.

In another embodiment of the invention, the system includes an insufflation conduit for delivering a continuous flow of insufflation gas to the body cavity at a flow rate through a flow path that communicates with a pneumatically sealed trocar which prevents over-pressurization of the body cavity, and an insufflator for driving gas flow through the insufflation conduit at a driving pressure, wherein the system can be configured so that either the gas flow rate through the insufflation conduit or the driving pressure required to maintain the specified flow rate can vary depending upon body cavity pressure.

When the system is configured so that the gas flow rate through the insufflation conduit varies depending upon body cavity pressure, the flow rate of the insufflation gas will be variable and the driving pressure of the insufflation gas will be specified. When system is configured so that the driving pressure that is required to maintain the specified flow rate varies depending upon body cavity pressure, the flow rate of the insufflation gas will be specified and the driving pressure of the insufflation gas will be variable.

These and other features of the multimodal gas delivery system of the subject invention will become more readily apparent to those having ordinary skill in the art from the following enabling description of the preferred embodiments of the subject invention taken in conjunction with the several drawings described below.

BRIEF DESCRIPTION OF THE DRAWINGS

So that those having ordinary skill in the art will readily understand how to make and use the gas delivery systems and methods of the subject invention without undue experimentation, preferred embodiments thereof will be described in detail herein below with reference to the figures wherein.

DETAILED DESCRIPTION OF THE EMBODIMENTS

Figure 1:
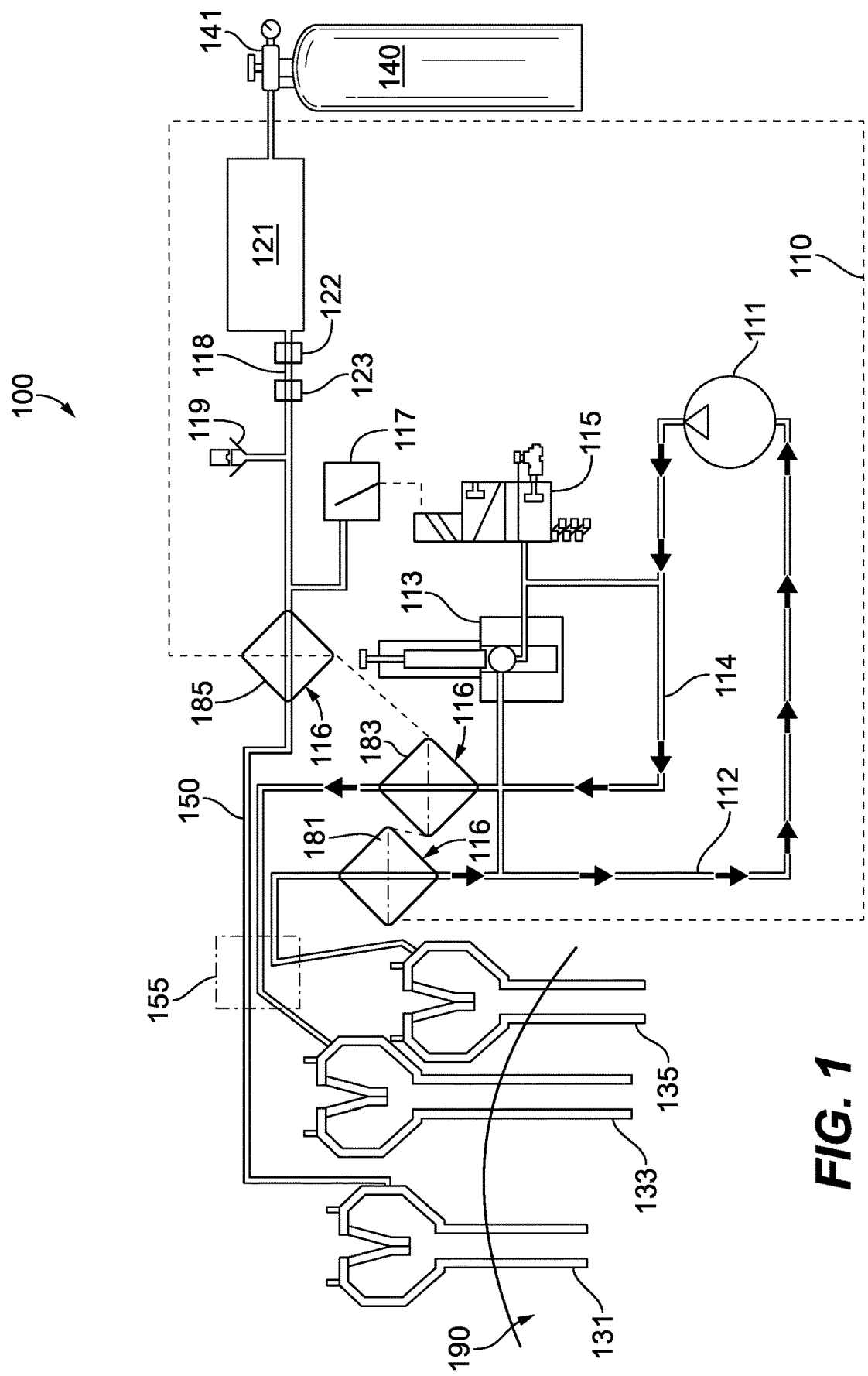
FIG. 1 is a schematic illustration of a multimodal surgical gas delivery system constructed in accordance with an embodiment of the subject invention which is configured for continuous pressure monitoring of a continuous flow of gas to a body cavity.

Referring now to the drawings, wherein like reference numerals identify similar structural elements or features of the subject invention, there is illustrated in FIG. 1 a multimodal surgical gas delivery system constructed in accordance with a preferred embodiment of the subject invention and designated generally by reference numeral 100. As described in more detail below, the gas delivery system 100 is designed for multimodal operation to facilitate insufflation of a body cavity, smoke evacuation from the body cavity and/or gas recirculation through an access port communicating with the body cavity. In addition, the surgical gas delivery system 100 is configured to maintain body cavity pressure when suction is used within the body cavity during a surgical procedure to remove solid debris, liquids and gases from the body cavity.

As shown in FIG. 1, the gas delivery system 100 is adapted to function with three surgical access devices or trocars (131, 133, 135) that are in communication with a patient's body cavity 190. It is envisioned that gas delivery system 100 can also be used with two surgical access devices or trocars, as disclosed for example in commonly assigned U.S. Pat. No. 9,375,539. Alternatively, the system can be employed with a single surgical access device as disclosed for example in commonly assigned U.S. Pat. No. 9,295,490.

Figure 2:
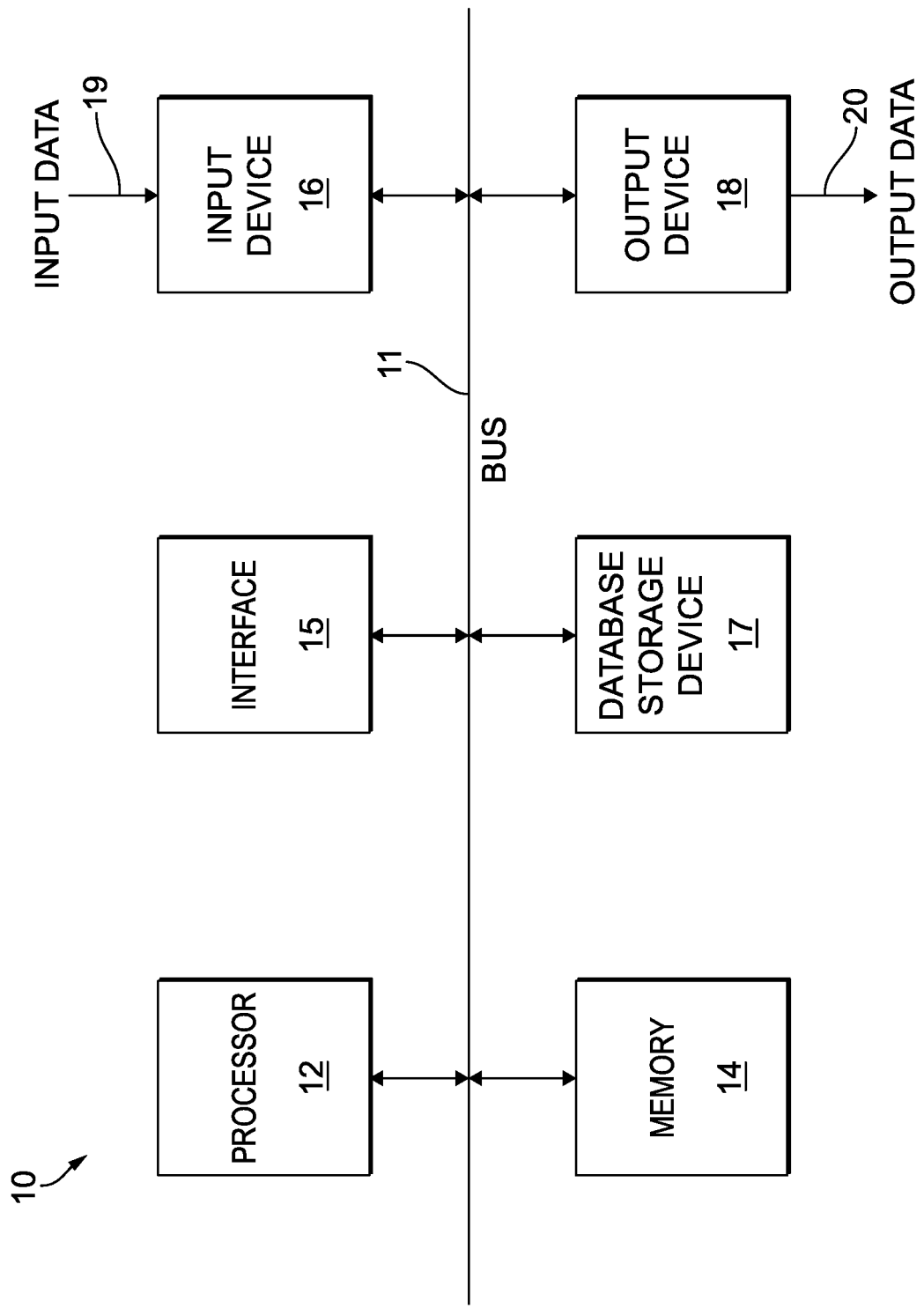
FIG. 2 is a schematic flow diagram of a computing environment that forms part of the multimodal surgical gas delivery system of FIG. 1.

The multimodal gas delivery system 100 includes a computer-controlled control unit 110 which is driven by a general purpose computing system that is best seen in FIG. 2. It is to be understood and appreciated that the computing system facilitates the selective modes of operation of multimodal gas delivery system 100.

Referring to FIG. 2, the computing system 10 of control unit 110 includes at least one processor 12, a memory 14, at least one input device 16 and at least one output device 18, which are all coupled together via a bus 11. The storage device 14 can be any form of data or information storage means, for example, volatile or non-volatile memory, solid state storage devices or magnetic devices.

In certain embodiments of the invention, input device 16 and output device 18 could be the same device. An interface 15 can also be provided for coupling the computing system 10 to one or more peripheral devices. For example interface 15 could be a PCI card or PC card. The memory or storage device 14 can house or maintain at least one database 17. The memory 14 can be any form of memory device, for example, volatile or non-volatile memory, solid state storage devices, or magnetic devices.

Input device 16 receives input data 19 and can comprise, for example, a keyboard, a pointer device such as a pen-like device, a mouse, a touch screen, or any other suitable device, such as a modem or wireless data adaptor, or data acquisition card. Input data 19 could come from different sources, for example keyboard instructions in conjunction with data received via a network.

Output device 18 produces or generates output data 20 and can comprise, for example, a display device or monitor in which case output data 20 is visual. Output data 20 could be distinct and derived from different output devices, for example a visual display on a monitor in conjunction with data transmitted to a network. A user could view data output, or an interpretation of the data output, on, for example, a monitor or using a printer.

In use, the computing system 10 is adapted to allow data or information to be stored in and/or retrieved from, via wired or wireless communication means, at least one database 17 stored in memory 14. The interface 15 may allow wired and/or wireless communication between the processing unit 12 and peripheral components that may serve a specialized purpose.

Preferably, the processor 12 receives instructions as input data 19 via input device 16 and can display processed results or other output to a user by utilizing output device 18. More than one input device 16 and/or output device 18 can be provided. It should be appreciated that the computing system 10 may be in any form, but it is preferably provided integral with the control unit 110 of surgical gas delivery system 100.

It is to be appreciated that the computing system 10 may be a part of a networked communications system. Computing system 10 could connect to a network, for example the Internet or a WAN. Input data 19 and output data 20 could be communicated to other devices via the network. The transfer of information or data over the network can be achieved using wired communications means or wireless communications means. A server can facilitate the transfer of data between the network and one or more databases. A server and one or more databases provide an example of an information source.

Thus, the computing system 10 may operate in a networked environment using logical connections to one or more remote computers. The remote computer may be a personal computer, a server, a router, a network PC, a tablet device, a peer device, or other common network node, and typically includes many or all of the elements described above.

Referring once again to FIG. 1, the multimodal surgical gas delivery system 100 includes a fluid pump 111 that is adapted and configured to circulate pressurized insufflation fluid through the system 100. A supply conduit 114 is in fluid communication with an output of the fluid pump 111 and it is configured and adapted for delivering pressurized insufflation fluid to an output port 183 of the control unit 110.

A return conduit 112 is in fluid communication with an input of the fluid pump 111 for delivering insufflation fluid to the fluid pump 111, and it is configured and adapted for returning insufflation fluid to an input port 181 of the control unit 110. An adjustable back-pressure control valve 113 is provided in fluid communication with the supply conduit 114 and the return conduit 112, and is adapted and configured to respond to a supply conduit pressure exceeding a set pressure, by opening and directing fluid from the supply conduit 114 to the return conduit 112. The back-pressure control valve 113 can be a mechanical valve, such as a resiliently-biased valve. Alternatively, the back-pressure control valve 113 can be an electro-mechanical valve, responding to a high pressure signal from one or more pressure sensors (e.g. 117) within the system 100.

An insufflation subunit 121 is provided and it is adapted and configured to receive a supply of insufflation gas (e.g., carbon dioxide) from a source 140 such as a local tank as shown or from a central distribution system, which may also pass through a pressure regulator 141 prior to entering the gas delivery system 100. The insufflation subunit 121 delivers insufflation gas to the rest of the system 100 through an insufflation conduit 118. The insufflation subunit 121 includes an internal pressure sensor (not shown) that senses the pressure of surgical cavity 190 through the insufflation conduit 118.

The gas delivery system 100 is operated or otherwise controlled by a user through a control panel, such as one provided on or otherwise in connection with the control unit 110. Such a control panel is preferably adapted and configured to permit a user to select a mode for the multimodal surgical gas delivery system, such as by way of a switch, touch screen or other user interface. For example a graphical user interface (GUI) can be provided that permits the selection of an operating mode as well as the operational parameters for a particular mode. It is to be understood and appreciated that the control panel may be provided integral with the system 100 or it can be remotely located therefrom using known means of data communication.

Operating modes can include, but are not limited to, insufflation, smoke evacuation, combined smoke evacuation and insufflation, recirculation, or combined recirculation and smoke evacuation. Operating parameters for a mode can include, for example, flow rate (e.g., liters/minute), pressure (e.g., mmHg), and conditioning parameters (e.g., temperature and humidity), and the like.

As used herein, the "recirculation" mode, alone or combined with other modes, is one that is suitable for providing sufficient operating pressures and flow rates to drive pneumatically sealed surgical access devices such as those described in commonly assigned U.S. Pat. Nos. 7,854,724 and 8,795,223, incorporated herein by reference.

A tube set 150 is also provided and it is adapted and configured to connect at one end to the supply conduit 114, return conduit 112 and insufflation conduit 118, and at the opposing end to a plurality of surgical access devices 131, 133, 135, which are in fluid communication with the surgical cavity 190. The configuration of the tube set 150 can vary, depending on the desired implementation, as mentioned above. In the case of the system 100, the tube set 150 preferably has a unitary, multi-lumen connection to input 181, output 183 and insufflation 185 ports, and separate connections to the individual surgical devices 131, 133, 135.

It is envisioned that the tube set 150 can have a compound, multi-lumen tube, beginning at the connections to the ports 181, 183, 185 for a predetermined distance from the control unit 110, and at an intermediate point a furcation 155 yields multiple separate tubes. In the case of the system 100, three separate tubes, separately lead to each of the surgical devices 131, 133, 135, which may be surgical access devices with insufflation capability, or other instruments, such one or more veress needles. The surgical devices 131, 133, 135 are thus individually connected to one of the supply conduit 114, return conduit 112 and insufflation conduit 118, and therefore respectively facilitate that function.

As set forth above, in one preferred aspect, the separate distal tube portions of the tube set 150 are connected by way of a conventional fitting, such as a luer-lock fitting on a conventional surgical device. The precise configuration of the tube set 150 can vary depending on the desired configuration. An example of a fitting for a multi-lumen tube set is described in commonly assigned U.S. Pat. No. 9,526,886, the disclosure of which is herein incorporated by reference in its entirety.

A disposable filter 116 is also associated with the tube set 150, either separate therefrom or integral therewith. A filter suitable for use with a multimodal gas delivery system 100 with insufflation, smoke evacuation and recirculation functionality for use with specialized pneumatically sealed surgical access devices is disclosed in U.S. Pat. Nos. 9,067,030 and 9,526,849, the disclosures of which are herein incorporated by reference in their entireties.

It is envisioned that the disposable tube sets 150 and/or filters 116 used in connection with the system 100, can be provided with identification devices that permit authorized use or otherwise prevent unauthorized use. Such identification devices can include, but are not limited to, a radiofrequency identification (RFID) transponder, computer readable data chip, bar code or other data-carrying element provided thereon. It is also envisioned that the identification device on the filter or tube set could cause or otherwise instruct the gas delivery system 100 to automatically switch into or launch in a particular operating mode (e.g., recirculation, smoke evacuation, or standard insufflation).

With continuing reference to FIG. 1, system 100 further includes a second dump valve 115 in connection with the fluid supply conduit 114. In addition, to the short-circuiting action of the back-pressure control valve 113 described above, the system 100 is provided with a pressure sensor 117, which can be mechanical or electronic as illustrated. Sensor 117 is in fluid communication with the insufflation conduit 118 or other source of abdominal pressure. When an over-pressure condition is sensed, the pressure sensor 117 signals the dump valve 115 to release fluid out of the system 100.

System 100 can be employed with one surgical device 131 being used for insufflation and sensing functions, and another surgical device 135 serving to remove insufflation gas from the abdomen, which then passes through a filter, such as an ultralow-penetration air ("ULPA") filter element 116 for example, before returning to the pump 111. The filter 116 is preferably configured and adapted to clear all or essentially all smoke and debris from the gas passing therethrough, with the gas being returned to the abdominal cavity 190 through a third surgical device 133. As illustrated, another filter element 116 can be provided in connection with the supply conduit 114 leading from the pump 111.

Figure 3:
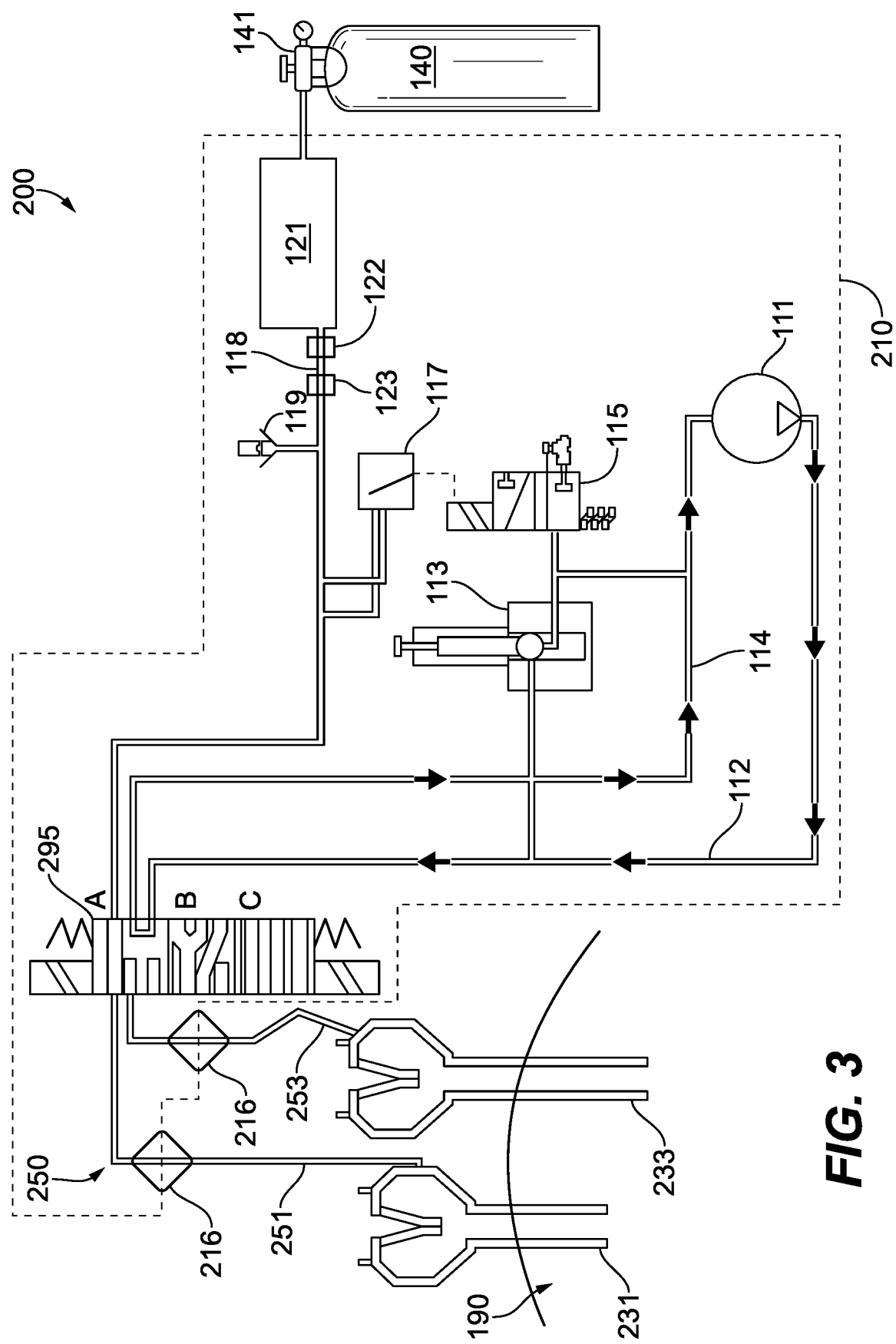
FIG. 3 is a schematic illustration of a multimodal surgical gas delivery system constructed in accordance with another embodiment of the subject invention which is configured for continuous pressure monitoring of a continuous flow of gas to a body cavity.

For the purposes of explanation and illustration, and not limitation, a schematic illustration of an exemplary embodiment of a surgical gas delivery system in accordance with another aspect of the subject invention is shown in FIG. 3 and is designated generally by reference numeral 200. As compared with the system 100 of FIG. 1 the system 200 only requires two surgical devices 231, 233. The functionalities of components described above in connection with the system 100 of FIG. 1 are the same as the corresponding components of the system 200 of FIG. 2, unless otherwise specified below.

The system 200 is in many ways similar to the system 100, but with the addition of a diverting valve 295, having three conduits 112, 114, 118 leading from other active internal system components, and two conduits 251, 253 leading, respectively, to two different surgical devices 231, 233.

As illustrated, the diverting valve 295 is provided integrally, within the control unit 210, as indicated schematically by placement of broken line referenced by number 210. The diverting valve 295 is provided with three operating positions—positions, A, B and C, corresponding to different functions, as described below. When the sensing function of the system 200 is active, the diverting valve 295 is positioned in, position "A", permitting connection of the insufflation/sensing conduit 118 therethrough, through one or both of the conduits 251, 253 of the tube set 250, and to one or both of the surgical devices 231, 233.

If configured to connect the insufflation/sensing conduit 118 to more than one surgical device, the potential for a lumen of such surgical device being blocked and thus not providing an accurate reading, is reduced. When the diverting valve 295 is positioned at position A, and connects the insufflation/sensing conduit 118 to the conduits 251, 253 of the tube set 250 and thus to the surgical devices 231, 233, the insufflator subunit 121 is permitted to sense the abdominal pressure. In position A, output from the pump 111 enters the diverting valve 295 and is returned to the pump 111 immediately by mutually connecting the supply conduit 114 and return conduit 112 under such circumstances. This configuration allows the pump 111 to continue running during sensing and thus avoids any power spikes which might occur if stopping and restarting of the pump 111.

If the system 200 is set to a suitable mode (such as combined smoke evacuation and insufflation), when the insufflator subunit 121 is finished sensing the abdominal pressure, the diverting valve 295 is switched from position A, to Position B, in order to connect the supply conduit 114 to a corresponding conduit 251 of the tube set 250, and the return conduit 112 to a corresponding conduit 253 of the tube set 250. In position B, the insufflator conduit 118 is connected to the return conduit 112, permitting addition of insufflation gas into the system 200 through the return conduit 112. Concurrently, the insufflator subunit 121 can be set to insufflating mode only, therefore only adding gas to the system 200 and not sensing pressures. While in position B, the diverting valve 295 permits delivery and return of fluid therethrough, between the pump 111 and filters 216, and the surgical devices 231, 233, and therefore gas exchange with, and filtration of, insufflation gasses from the surgical cavity 190.

If the pump and tube volume are considered as one controlled volume in conjunction with the volume of the surgical cavity 190, the function of the insufflator subunit 121 alone—switching from sensing to supplying carbon dioxide—is performed as in conventional surgical insufflators, in accordance with a preferred aspect. Accordingly, as described above, in system 200 of FIG. 3, smoke evacuation and filtration is only performed when the diverting valve 295 permits the insufflator control 121 to provide gas to the surgical cavity 190. In such an arrangement, toggling to and from smoke evacuation/filtration and pressure sensing can be configured as either a normally sensing mode, or as a normally filtering mode, as desired or required. A normally sensing mode is likely to be preferred over a normally filtering mode, as monitoring of abdominal pressures is typically a priority.

As illustrated, position C of the diverting valve 295 permits the system 200 to be operated in a recirculation mode, which is suitable for providing sufficient pressures and flow rates to drive pneumatically sealed surgical access devices such as those described in U.S. Pat. Nos. 7,854,724 and 8,795,223, for example. In such a mode, a single tube of three lumens is typically provided, one lumen being in fluid communication with each of the supply conduit 112, return conduit 114 and the insufflation conduit 118.

In certain applications, it is advantageous to monitor pressure at the surgical cavity 190, in real time, during insufflation. Real time pressure monitoring helps to better detect and respond to changes in pressure the surgical cavity. Furthermore, continuous pressure monitoring in conjunction with the consistent flow of new or recirculated insufflation gas also facilitate improved smoke removal from the surgical cavity.

With continuing reference to FIGS. 1-3, systems 100, 200 include a flow meter 123 positioned between the insufflation gas source 140 and the abdominal cavity 190. Flow meter 123 measures the fluid flow through the associated insufflation conduit 118. Monitoring of abdominal pressure in real time is accomplished by driving fluid flow through the conduit 118 at a constant source pressure by regulating the pressure provided from source 140 using insufflation subunit 121.

As the amount of fluid flowing through conduit 118 varies, depending upon the amount of pressure at the surgical cavity 190, the flow meter 123 measures the fluid flow. The processor 12 of system 100, 200 uses the fluid flow reading from flow meter 123 to determine pressure at the surgical cavity 190, for a given source pressure provided by source 140. Pressure at the surgical cavity 190 can be determined by the processor 12 using data stored in memory 14 of system 100, 200, for example, in a look up table, or through calibration of the fluid path to the surgical cavity 190, or a combination of both. When using data stored in memory 14 of system 100, 200 the appropriate data is selected by the processor 12 based on the known dimensions of a portion of the fluid path to the surgical cavity 190, for example, the luer connection to a trocar or cannula connecting the surgical cavity 190 to system 100, 200.

Figure 4:
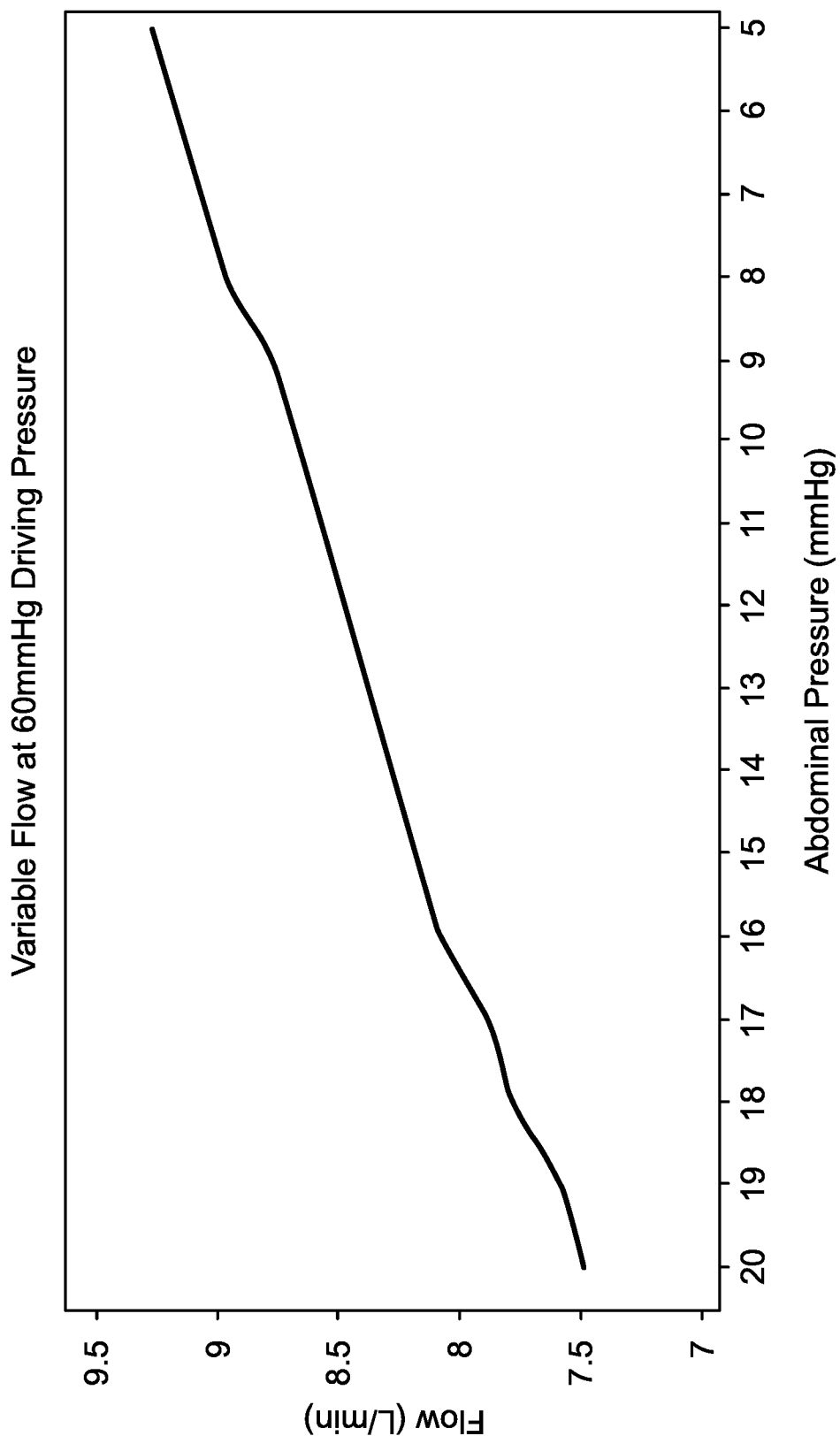
FIG. 4 is a graphical illustration of a look up table for insufflation gas delivered by the multimodal gas delivery system of the subject invention at a variable flow and a specified driving pressure of 60 mmHg.

The known dimensions of the portion of the fluid path, in this instance the trocar or cannula luer connection, can be an industry standard, for example, ISO 594-1:1986 or ISO 594-2:1998, or known dimensions of a compatible component, for example, one of the trocars disclosed in U.S. Pat. No. 7,854,724, or 8,795,223, the disclosures of which are incorporated herein in their entireties. The known dimensions permit assumptions to be made as to the amount of flow through that portion of the fluid path for a given driving pressure, which in turn can be used to infer pressure at the surgical cavity 190 using, for example, a look up table stored in the memory 14 of system 100, 200. FIG. 4 illustrates an example of a look up table for a driving pressure of 60 mm of Hg at a variable flow rate provided by insufflation gas source 140.

When the fluid path does not include known dimensions, pressure at the surgical cavity 190 can be determined by the processor 12 of system 100, 200 using a calibration algorithm. When calibration algorithm is used, system 100, 200 senses pressure at surgical cavity 190, for example, using the pressure sensor included in insufflation subunit 121 or using a dedicated pressure sensor 122 positioned along the fluid path to the surgical cavity 190. Calibration can be accomplished by taking periodic static pressure measurements using one of the pressure sensors described above and associating those pressure measurements with the periodic flow measurements taken using the flow meter 123. In certain situations, it can be advantageous to combine calibration with the inferring technique described above.

Alternatively, monitoring of abdominal pressure in real time can be accomplished by driving fluid flow through the conduit 118 at a variable source pressure by regulating the pressure provided from source 140 using insufflation subunit 121. The amount of fluid flow through conduit 118 is specified and maintained using a feedback from flow meter 123 to the insufflation subunit 121. The amount of source pressure needed to maintain the specified flow through the fluid path depends on the amount of pressure at the surgical cavity 190. A pressure sensor, for example, the pressure sensor included in insufflation subunit 121 or one, for example, pressure sensor 122, positioned along the fluid path to the surgical cavity 190, for example, near the pressure source or subunit 121, measures the variable source pressure required to maintain the specified flow through the fluid path.

In this embodiment, pressure at the surgical cavity 190 can be determined by the processor 12 using data stored in memory 14 of system 100, 200 for example, in a look up table, or through calibration of the fluid path to the surgical cavity 190, or a combination of both. When using data stored in system 100, the appropriate data is selected based on the known dimensions of a portion of the fluid path to the surgical cavity 190, for example, the luer connection to a trocar or cannula connecting the surgical cavity 190 to system 100, 200. The known dimensions of the portion of the fluid path, in this instance the trocar or cannula luer connection, can be an industry standard, for example, ISO 594-1:1986 or ISO 594-2:1998, or known dimensions of a compatible component, for example, one of the trocars disclosed in U.S. Pat. Nos. 9,095,372, 7,854,724, or 8,795,223, the disclosures of which are incorporated herein in their entireties.

Figure 5:
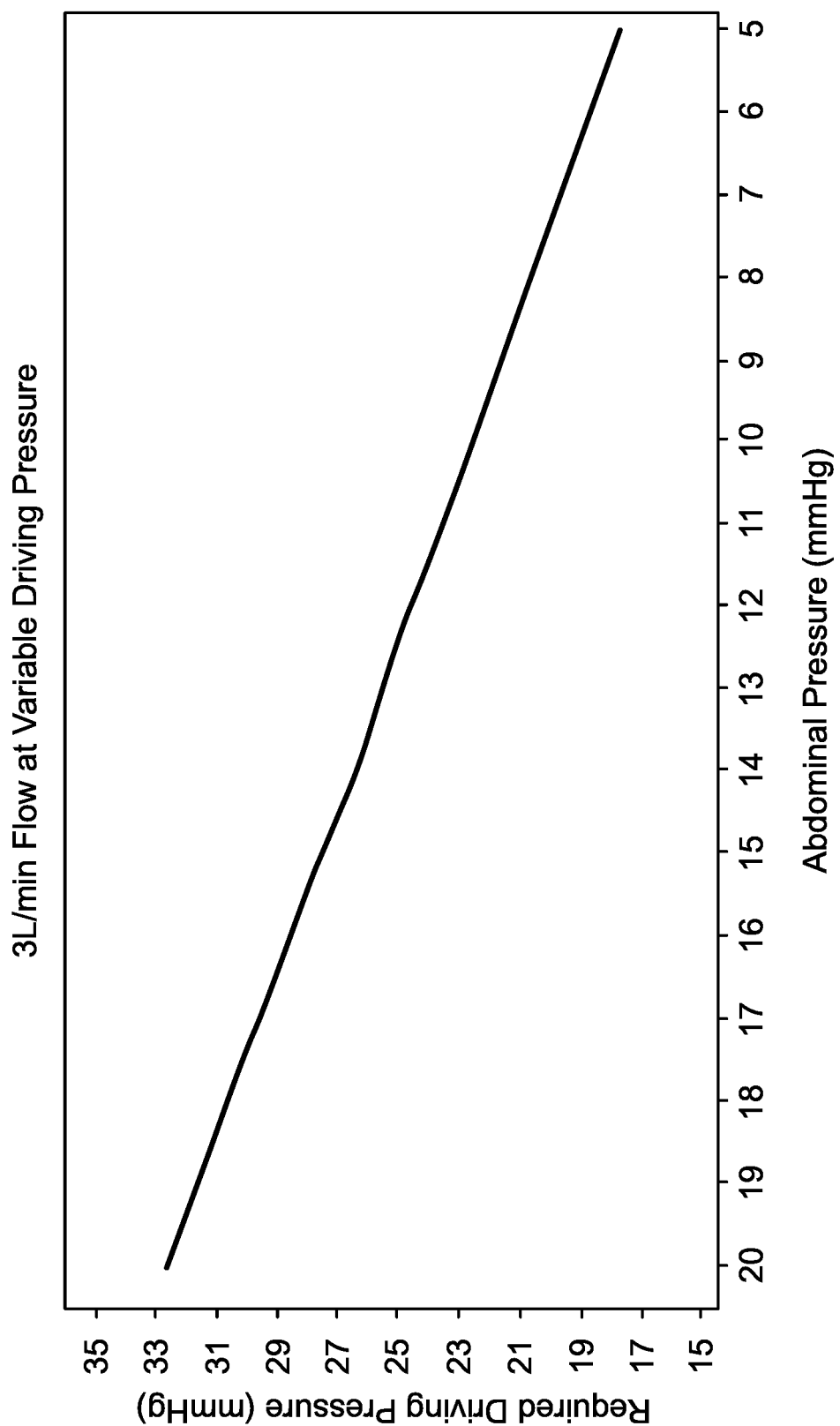
FIG. 5 is a graphical illustration of a look up table for insufflation gas delivered by the multimodal gas delivery system of the subject invention at a specified flow of 3 L/min and a variable driving pressure.

The known dimensions permit assumptions to be made as to the amount of source pressure needed to maintain the specified fluid flow through that portion of the fluid path, which in turn can be used to infer pressure at the surgical cavity 190 using, for example, a look up table stored in system 100. FIG. 5 illustrates an example of a look up table for a specified fluid flow of 3 L/minute through the fluid path.

When the fluid path does not include known dimensions, pressure at the surgical cavity 190 can be determined using a calibration algorithm. When calibration algorithm is used, system 100, 200 senses pressure at surgical cavity 190, for example, using the pressure sensor included in insufflation subunit 121 or using a dedicated pressure sensor, for example, pressure sensor 122, positioned along the fluid path to the surgical cavity 190. Calibration can be accomplished in processor 12 of system 100, 200 by taking periodic static pressure measurements using one of the pressure sensors described above and associating those pressure measurements with corresponding driving pressures regulated by subunit 121. In certain applications, it can be advantageous to combine calibration with the inferring technique described above for a specific fluid flow.

While the subject disclosure has been shown and described with reference to preferred embodiments, those skilled in the art will readily appreciate that changes and/or modifications may be made thereto without departing from the scope of the subject disclosure.

What is claimed is:

1. A system for delivering insufflation gas to a body cavity of a patient during an endoscopic surgical procedure, comprising:
    a) an insufflation conduit for delivering a continuous flow of insufflation gas to the body cavity at a variable flow rate through a flow path that includes a pneumatically sealed trocar which prevents over-pressurization of the body cavity;
    b) an insufflator for driving gas flow through the insufflation conduit at a specified driving pressure, wherein the gas flow rate through the insufflation conduit will vary depending upon body cavity pressure;
    c) a flow meter communicating with the insufflation conduit and located between the insufflator and the body cavity for continuously measuring gas flow through the insufflation conduit, wherein a driving pressure sensor is located between the flow meter and the insufflator for providing feedback to the insufflator so that the insufflator maintains the specified driving pressure of insufflation gas to the insufflation conduit; and
    d) a processor for determining a body cavity pressure corresponding to a given driving pressure based upon a gas flow measurement from the flow meter, wherein the processor utilizes known dimensions of the pneumatically sealed trocar stored in memory in a look up table with data for a continuous flow of insufflation gas delivered at a variable flow rate and a specified driving pressure to infer the body cavity pressure, and when the dimensions of the pneumatically sealed trocar are unknown, the processor determines body cavity pressure by taking periodic static pressure measurements from a second pressure sensor located in the flow path downstream from the flow meter, and associating the periodic static pressure measurements with periodic flow measurements taken by the flow meter.

2. The system of claim 1, wherein the known dimensions of the pneumatically sealed trocar relate to a luer connection of the trocar.

3. The system of claim 1, wherein the look up table includes data for a continuous flow of insufflation gas delivered at a variable flow rate and a specified driving pressure of 60 mmHg to infer the body cavity pressure.

4. A system for delivering insufflation gas to a body cavity of a patient during an endoscopic surgical procedure, comprising:
    a) an insufflation conduit for delivering a continuous flow of insufflation gas to the body cavity at a specified flow rate through a flow path that includes a pneumatically sealed trocar which prevents over-pressurization of the body cavity;
    b) an insufflator for driving gas flow through the insufflation conduit at a variable driving pressure, wherein the driving pressure required to maintain the specified flow rate will vary depending upon body cavity pressure;
    c) a driving pressure sensor communicating with the insufflation conduit and located between the insufflator and the body cavity for continuously measuring variable driving pressure in the insufflation conduit; and
    d) a processor for determining an amount of driving pressure required to maintain the specified flow rate of insufflation gas to the body cavity through the flow path, wherein the processor utilizes known dimensions of the pneumatically sealed trocar stored in memory in a look up table with data for a continuous flow of insufflation gas delivered at a specified flow rate and a variable driving pressure to infer the body cavity pressure, and when the dimensions of the pneumatically sealed trocar are unknown, the processor determines body cavity pressure by taking periodic static pressure measurements from a second pressure sensor located in the flow path and associating the periodic static pressure measurements with corresponding driving pressures regulated by the insufflator.

5. The system of claim 4, wherein the known dimensions of the pneumatically sealed trocar relate to a luer connection of the trocar.

6. The system of claim 4, wherein the look up table includes data for a continuous flow of insufflation gas delivered at a specified flow rate of 3 L/min and a variable driving pressure to infer the body cavity pressure.

* * * * *